United States Patent
Yoo et al.

(10) Patent No.: US 7,259,272 B2
(45) Date of Patent: Aug. 21, 2007

(54) ω-[2-(POLYALKYLENEOXY)ETHYLTHIO] ALKYLALKOXYSILANE DERIVATIVE AND PREPARATION METHOD THEREOF

(75) Inventors: Bok Ryul Yoo, Seoul (KR); Joon Soo Han, Seongnam-si (KR); Weon Cheol Lim, Seoul (KR); Joo-hyun Cho, Suwon-si (KR); Yoo Kyoung Jeon, Hanam-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 11/314,423

(22) Filed: Dec. 20, 2005

(65) Prior Publication Data
US 2007/0043232 A1 Feb. 22, 2007

(30) Foreign Application Priority Data
Aug. 17, 2005 (KR) ...................... 10-2005-0075265

(51) Int. Cl.
C07F 7/04 (2006.01)
(52) U.S. Cl. ..................................... 556/427
(58) Field of Classification Search ............... 556/427
See application file for complete search history.

(56) References Cited
FOREIGN PATENT DOCUMENTS
EP 0 387 689 A 9/1990
JP DD129446 * 10/1980

OTHER PUBLICATIONS

Ritchie et al (Analytica Chimica Acta 496 pp. 65-71, 2003).*
Lecamp et al ( Eur. Poly. J. vol. 33, No. 7 pp. 1021-1029, 1997.*
Chem Abtract; 1981:122910, Abstract of JP55129446, Oct. 1980.*
A. Kh. Sharipov; "Oxidation of Sulfides with Hydrogen Peroxide to Sulfoxides and Sulfones"; *Organic Synthesis and Industrial Organic Chemistry; Russian Journal of Applied Chemistry*, vol. 76, No. 1, 2003, pp. 108-113.

* cited by examiner

*Primary Examiner*—Samuel Barts
(74) *Attorney, Agent, or Firm*—Frommer Lawrence & Haug LLP; Ronald R. Santucci

(57) ABSTRACT

The present invention relates to a ω-[2-(polyalkyleneoxy) ethylthio]alkylalkoxysilane derivative and a preparation method thereof, more particularly to a ω-[2-(polyalkyleneoxy)ethylthio]alkylalkoxysilane derivative prepared by transforming a (ω-mercaptoalkyl)alkylalkoxysilane compound into a ω-(alkoxysilyl)alkylthiolate metal salt by treating it with a metallic base and performing dehalometallation at low reaction temperature using a poly(alkyleneoxy)alkyl ether halide or a poly(alkyleneoxy)bis(haloalkyl) ether to form a carbon-sulfur bond and a preparation method thereof. The novel compound of the present invention has not only a Si—OR bond but also contains a sulfur atom in the molecule, so that it can be used as monomer for synthesizing hydrophilic functional silicon polymers, source material of silicon-based surfactants and surface modifier of organic/inorganic materials. In addition, the preparation method of the compound is an economical one as the reaction can be performed at room temperature, the production yield is high and the reaction byproduct (metal halide) can be easily removed by filtration.

7 Claims, No Drawings

ω-[2-(POLYALKYLENEOXY)ETHYLTHIO]ALKYLALKOXYSILANE DERIVATIVE AND PREPARATION METHOD THEREOF

CROSS REFERENCE TO RELATED APPLICATION

This application is based on, and claims priority from Korean Patent Application No. 10-2005-0075265, filed on Aug. 17, 2005, the disclosure of which is hereby incorporated by reference.

TECHNICAL FIELD

The present invention relates to a ω-[2-(polyalkyleneoxy)ethylthio]alkylalkoxysilane derivative and a preparation method thereof, more particularly to a ω-[2-(polyalkyleneoxy)ethylthio]alkylalkoxysilane derivative having a novel structure represented by formula 1 below, which is prepared by transforming a (ω-mercaptoalkyl)alkylalkoxysilane compound to a ω-(alkoxysilyl)alkylthiolate metal salt using a metallic base and forming a carbon-sulfur bond by dehalometallation with a poly(alkyleneoxy)alkyl ether halide or a poly(alkyleneoxy)bis(haloalkyl) ether at low temperature, and a preparation method thereof:

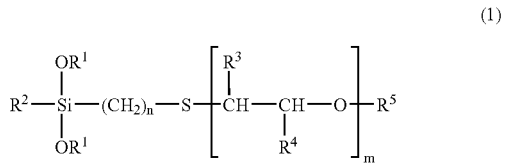

(1)

where $R^1$ is $C_1$-$C_6$ alkyl or phenyl; $R^2$ is $C_1$-$C_6$ alkyl, $C_1$-$C_6$ alkoxy, phenyl or phenoxy; each of $R^3$ and $R^4$ is hydrogen or $C_1$-$C_6$ alkyl; $R^5$ is $C_1$-$C_{18}$ alkyl, alkyl having an aromatic group, $C_3$-$C_{18}$ cyclic alkyl, $C_2$-$C_{18}$ alkene having an unsaturated bond or —$CH_2CH_2S(CH_2)_nSiR^2(OR^1)_2$; n is an integer of 2 or 3; and m is an integer of 1 to 1,000.

Organic alkylalkoxysilane compounds having hydrophilic poly(ethyleneoxy) groups are industrially useful compounds used in manufacturing functional silicon polymers. Norio Kawai and Etsuko Takagi reported in 1990 that they synthesized a novel hydrophilic functional organosilane compound by reacting $HSi(R^1)_2OR^4$ ($R^1$=alkyl or alkoxy; $R^4$=alkyl) with an unsaturated ether compound [$R^4(OX)_m OR^8$ ($R^8$=$C_2$-$C_6$ alkenyl)] in the presence of platinum catalyst [European Patent Publication No. 387689 (1990)].

As in the method described above, organosilane compounds having hydrophilic functional groups are generally synthesized from hydrosilation of poly(ethyleneoxy)alkene with a silane compound having a Si—H bond in the presence of expensive platinum catalyst. The poly(ethyleneoxy)alkene, or the starting material, is synthesized from dehalometallation of haloalkene and a poly(ethyleneoxy) metal salt.

In such conventional process of manufacturing organosilane compounds having hydrophilic functional groups, poly(ethyleneoxy)alkene prepared from dehalometallation is hydrosilated with a silane compound having an Si—H in the presence of expensive platinum catalyst. However, this method is disadvantageous in that the carbon-carbon bonding for preparation of poly(ethyleneoxy)alkene requires high reaction temperature and takes long time. Also, it is difficult to re-collect the expensive platinum catalyst after hydrosilation.

On the other hand, the (ω-mercaptoalkyl)alkylalkoxysilane compound, or the starting material of the present invention, is easily transformed into a ω-(alkoxysilyl)alkylthiolate metal salt when treated with a metallic base under a mild reaction condition. And, since the alkylthiolate metal salt is much more reactive than general metal akoxides in nucleophilic substitution with a poly(alkyleneoxy)alkyl ether halide or a poly(alkyleneoxy)bis(haloalkyl) ether, carbon-sulfur bonding is formed easily even at room temperature. Thus, the method of the present invention is advantageous in that the ω-[2-(polyalkyleneoxy)ethylthio]alkylalkoxysilane derivative can be synthesized in good yield without using expensive platinum catalyst.

To date, synthesis of a ω-[2-(polyalkyleneoxy)ethylthio]alkylalkoxysilane compound having both sulfur atom and alkyleneoxy group by dehalometallation of a silylalkylthiolate metal salt, which is prepared by treating a (ω-mercaptoalkyl)alkylalkoxysilane compound with a metallic base, with a poly(alkyleneoxy)alkyl ether halide or a poly(alkyleneoxy)bis(haloalkyl) ether has not been known.

DISCLOSURE OF THE INVENTION

In an embodiment, the present invention provides a ω-[2-(polyalkyleneoxy)ethylthio]alkylalkoxysilane compound having a Si—OR bond in the molecule, so that a variety of functional groups can be introduced, and having a sulfur atom in the molecule, thereby having improved hydrophilicity. The novel compound of the present invention has a sulfur atom in the molecule, which is oxidized to sulfoxide (S═O) or sulfone (O═S═O) and, thereby, offers improved hydrophilicity.

In another embodiment, the present invention provides an economical preparation method of the ω-[2-(polyalkyleneoxy)ethylthio]alkylalkoxysilane derivative with novel structure.

BEST MODE FOR CARRYING OUT THE INVENTION

The present invention is characterized by a ω-[2-(polyalkyleneoxy)ethylthio]alkylalkoxysilane derivative represented by the following formula 1:

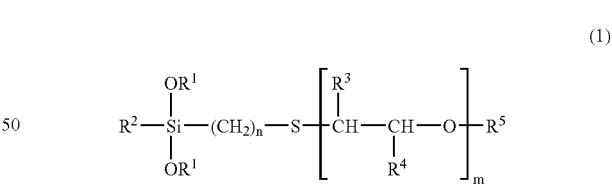

(1)

wherein $R^1$ is $C_1$-$C_6$ alkyl or phenyl; $R^2$ is $C_1$-$C_6$ alkyl, $C_1$-$C_6$ alkoxy, phenyl or phenoxy; each of $R^3$ and $R^4$ is hydrogen or $C_1$-$C_6$ alkyl; $R^5$ is $C_1$-$C_{18}$ alkyl, alkyl having an aromatic group, $C_3$-$C_{18}$ cyclic alkyl, $C_2$-$C_{18}$ alkene having an unsaturated bond or —$CH_2CH_2S(CH_2)_nSiR^2(OR^1)_2$; n is an integer of 2 or 3; and m is an integer of 1 to 1,000.

The present invention is also characterized by a method for preparing the ω-[2-(polyalkyleneoxy)ethylthio]alkylalkoxysilane derivative represented by the formula 1 below, which comprises the steps of:

transforming the (ω-mercaptoalkyl)alkylalkoxysilane compound represented by the formula 2 below to the ω-(alkoxysilyl)alkylthiolate metal salt represented by the formula 3 below by reacting it with an alkali metal or alkaline earth metal base; and dehalometallating it with the poly(alkyleneoxy)alkyl ether halide represented by the formula 4 or the poly(alkyleneoxy) bis(haloalkyl) ether represented by the formula 5 below:

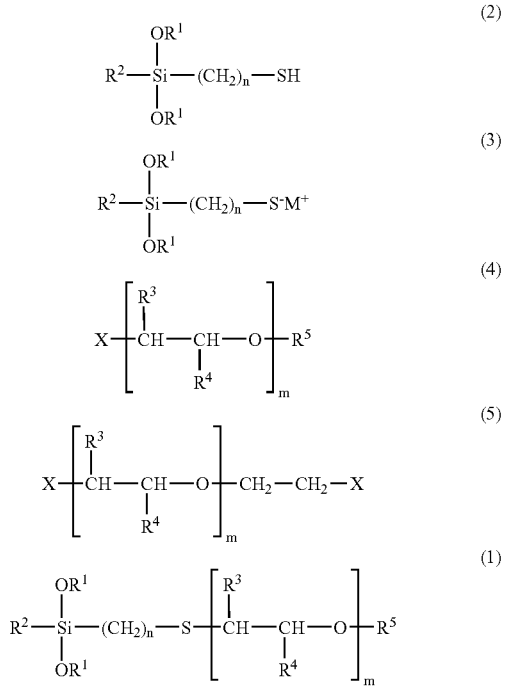

wherein each of $R^1$, $R^2$, $R^3$, $R^4$, $R^5$, m and n is the same as defined in the formula 1 above; and M represents an alkali metal or alkaline earth metal atom.

Hereunder is given a further detailed description of the present invention.

The present invention relates to a ω-[2-(polyalkyleneoxy)ethylthio]alkylalkoxysilane derivative having a novel structure, which has a sulfur atom and a Si—OR bond in the molecular structure, thereby having improved hydrophilicity and enabling introduction of a variety of functional groups, and thus being useful as source material of hydrophilic functional silicon polymers and silane-based binders, and a preparation method thereof.

Preferably, in the formula 1 representing the compound of the present invention, $R^1$ is $C_1$-$C_6$ alkyl; $R^2$ is $C_1$-$C_6$ alkyl or $C_1$-$C_6$ alkoxy; each of $R^3$ and $R^4$ is hydrogen or methyl; $R^5$ is $C_1$-$C_{18}$ alkyl, $C_1$-$C_{18}$ alkyl-substituted phenyl or —$CH_2CH_2S(CH_2)_n SiR^2(OR^1)_2$; n is an integer of 2 or 3; and m is an integer of 1 to 1,000.

The preparation method of the present invention is advantageous in that the (ω-mercaptoalkyl)alkylalkoxysilane represented by the formula 2, which is produced in industrial scale, is used as silane-based source material, dehalometallation can be performed at lower temperature, especially at room temperature, than conventional methods and metal halide byproducts (particularly NaCl) can be easily removed by filtration.

Especially, the present invention is advantageous in that, in transforming the (ω-mercaptoalkyl)alkylalkoxysilane represented by the formula 2 into the ω-(alkoxysilyl)alkylthiolate metal salt represented by the formula 3, or in transformation of a thiol (—SH) into a thiolate (—SM), alkali metal or alkaline earth metal compounds which are relatively stable can be used as a metallic base, not to mention highly reactive ones. That is, not only alkali metals or alkaline earth metals, but also their hydrides, alkyl compounds, alkoxide compounds, etc. can be used as a metallic base. Notably, alkoxide compounds of alkali metals or alkaline earth metals can be used as a metallic base. It is because the hydrogen of a thiol (—SH) is more acidic than that of an alcohol (—OH) in treatment with the metal alkoxide.

In the preparation method of the present invention, the carbon-sulfur bond is formed as the ω-(alkoxysilyl)alkylthiolate metal salt (formula 3) having a sulfur-metal (S-M) bond is dehalometallated with the poly(alkyleneoxy)alkyl ether halide (formula 4) or the poly(alkyleneoxy)bis(haloalkyl) ether compound (formula 5) having a carbon-halogen (C—X) bond. Since thiolate (—SM) acts as a stronger nucleophilic substitution reagent than alcoholate (—OM) in the nucleophilic substitution with the compound represented by the formula 4 or formula 5, reaction proceeds easily with such a relatively less reactive halide as alkyl chloride. In addition, the metal halide (MX) byproduct can be easily removed by filtration.

As a typical preparation method in accordance with the present invention, the (ω-mercaptoalkyl)alkylalkoxysilane compound represented by the formula 2 is put in a reaction flask inside a glass reactor connected with a dropping funnel and a condenser in nitrogen atmosphere. After adding a metallic base dropwise, the poly(alkyleneoxy)alkyl ether halide represented by the formula 4 or the poly(alkyleneoxy) bis(haloalkyl) ether compound represented by the formula 5 is added dropwise for reaction.

The metallic base and the compound represented by the formula 4 or 5 are used in the amount of from 0.4 to 1.2 moles, preferably in 1 mole, per 1 mole of the (ω-mercaptoalkyl)alkylalkoxysilane compound represented by the formula 2.

The preparation in accordance with the present invention does not necessarily require a reaction solvent. However, a polar organic solvent selected from alcohols such as methanol, ethanol and propanol, tetrahydrofuran, diethyl ether, acetonitrile, etc., may be used for more efficient reaction.

The transformation into the alkylthiolate metal salt and the dehalometallation are performed at a temperature of from −100° C. to 150° C., preferably 0° C. to 70° C. and particularly preferably at room temperature of 20° C. to 30° C.

After 1 to 24 hrs of reaction in the above condition, the reaction mixture is filtered to remove metal halide (MX) and used after fractional distillation or by itself.

The present invention is also characterized in that it is an economical one with good yield since the dehalometallation proceeds quantitatively. Separation of the metal halide from the reaction mixture can be performed as follows. First, the metal halide may be separated from the reaction product by distilling the reaction mixture at normal pressure or reduced pressure. Alternatively, the metal halide compound precipitated in the reaction mixture may be removed by filtering.

With a production yield of 90% or above, the above-mentioned method is highly economical.

Hereunder is given a detailed description of the starting materials and reactions employed in the present invention.

For the ω-(mercaptoalkyl)alkylalkoxysilane represented by the formula 2, one selected from (3-mercaptopropyl) methyldimethoxysilane, (3-mercaptopropyl)trimethoxysilane, (3-mercaptopropyl)methyldiethoxysilane, (3-mercaptopropyl)triethoxysilane, (2-mercaptoethyl)

methyldimethoxysilane, (2-mercaptoethyl)trimethoxysilane, (2-mercaptoethyl)methyldiethoxysilane, (2-mercaptoethyl)triethoxysilane, (3-mercaptopropyl)tripropoxysilane, etc. can be used.

For the metallic base, alkali metals such as lithium, sodium and potassium, alkaline earth metals such as magnesium and calcium, alkali metal hydrides such as lithium hydride, sodium hydride and potassium hydride, alkaline earth metal hydrides such as magnesium hydride and calcium hydride, $C_1$-$C_6$ alkyl alkali metal salts such as alkyl lithium, alkyl sodium and alkyl potassium, $C_1$-$C_6$ alkyl alkaline earth metal salts such as alkyl magnesium and alkyl calcium, $C_1$-$C_6$ alkali metal alkoxides such as lithium alkoxide, sodium alkoxide and potassium alkoxide or $C_1$-$C_6$ alkaline earth metal alkoxides such as magnesium alkoxide and calcium alkoxide may be used.

The poly(alkyleneoxy)alkyl ether halide represented by the formula 4 is a compound having ethyleneoxy or propyleneoxy groups with various degree of polymerization. Specific examples of the poly(alkyleneoxy)alkyl ether halide represented by the formula 4 are organic halides having ethyleneoxy groups with various degree of polymerization such as di(ethyleneoxy)methyl chloride, tris(ethyleneoxy)methyl chloride, tris(ethyleneoxy)methyl bromide, poly(ethyleneoxy)alkyl ether chloride, poly(ethyleneoxy)bis (chloroethyl) ether and poly(ethyleneoxy)bis(chloroalkyl) ether and poly(propyleneoxy)propyl chloride having propyleneoxy groups.

For the poly(alkyleneoxy)bis(haloalkyl) ether compound represented by the formula 5, poly(ethyleneoxy) compounds having α,ω-bis(chloroethyl) or α,ω-bis(chloroalkyl) terminal groups with ethyleneoxy groups of various sizes, such as di(ethyleneoxy) bis(chloroethyl) ether and poly(ethyleneoxy) bis(chloroalkyl) ether, may be used. Poly(propyleneoxy)propyl chloride having propyleneoxy groups may also be used.

In the compounds represented by the formulas 4 and 5, the halogen may be any one of chlorine, bromine or iodine. However, preferably chlorine compounds are preferably used because they are the most economical.

As described above, the preparation method of the present invention enables synthesis of various ω-[2-(polyalkyleneoxy)ethylthio]alkylalkoxysilane derivatives economically and effectively, compared with conventional preparation methods of organosilane compounds. Also, the preparation process is very simple and requires low cost.

And, the ω-[2-(polyalkyleneoxy)ethylthio]alkylalkoxysilane derivative prepared by the present invention can be widely used for synthesis of functional silicon polymers. Modified silicon compounds having hydrophilic functional substituents may be utilized as surfactants. Whereas conventional hydrophilic modified silicon compounds are mostly ones with substituted poly(ethyleneoxy) or poly(propyleneoxy) groups, the ω-[2-(polyalkyleneoxy)ethylthio]alkylalkoxysilane derivative of the present invention can be easily transformed into a hydrophilic sulfoxide by oxidizing the sulfur atom. It is reported that, in general, dimethyl sulfide is easily transformed to hydrophilic dimethyl sulfoxide at room temperature by treatment with hydrogen peroxide (A. Kh. Sharipov, *Russian Journal of Applied Chemistry*, 2003, 76, 108-113). Utilizing this property, the ω-[2-(polyalkyleneoxy)ethylthio]alkylalkoxysilane derivative represented by the formula 1 may be coated by chemical bonding on the surface, which may be further oxidized to obtain a more hydrophilic material.

Hereinafter, the present invention will be described in more detail through examples. Although the following examples describe only the uses of specific (ω-mercaptoalkyl)alkylalkoxysilane compound, alkoxy metal salt, poly(alkyleneoxy)alkyl ether chloride, etc., comparable effects can be attained with other equivalent compounds. Therefore, the scope of the present invention should not be limited to or by the following examples.

EXAMPLE 1

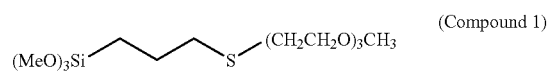

(Compound 1)

A 500 mL flask dried in an oven was equipped with a reflux condenser. To the flask were added 16.9 g (0.0861 mol) of (3-mercaptopropyl)trimethoxysilane and 150 mL of tetrahydrofuran under nitrogen atmosphere. The flask was cooled with ice water and stirred for 10 min after adding 35.9 mL (0.0861 mol) of 2.40 M sodium methoxide solution. 15.0 g (0.0820 mol) of tris(ethylene glycol)methyl ether chloride was added for 10 min and the temperature was increased to room temperature. The mixture was stirred for 1 hr at room temperature and the product was filtered. The solvent was removed at normal pressure and the residue was distilled in vacuum to obtain 25.4 g of the compound 1 (yield: 90%).

Compound 1: b.p. 146.5° C./0.5 mmHg; $^1$H NMR (CDCl$_3$, 300 MHz), δ (ppm) 0.70 (t, J=7.9 Hz, 2 H, SiCH$_2$), 1.60-1.70 (m, 2 H, SiCH$_2$CH$_2$), 2.52 (t, J=7.5 Hz, 2 H, SiCH$_2$CH$_2$CH$_2$), 2.66 (t, J=7.2 Hz, 2 H, SCH$_2$CH$_2$O), 3.34 (s, 3 H, CH$_3$O), 3.52 (s, 9 H, CH$_3$OSi), 3.50-3.63 (m, 10 H, CH$_2$O).

EXAMPLE 2

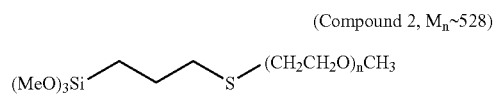

(Compound 2, $M_n$~528)

A 500 mL flask dried in an oven was equipped with a reflux condenser. To the flask were added 14.0 g (0.0713 mol) of (3-mercaptopropyl)trimethoxysilane and 150 mL of tetrahydrofuran under nitrogen atmosphere. The flask was cooled with ice water and stirred for 10 min after adding 29.7 mL (0.0713 mol) of 2.40 M sodium methoxide solution. 23.1 g (0.0626 mol) of poly(ethylene glycol)methyl ether chloride ($M_n$~369) was added for 10 min and the temperature was increased to room temperature. The mixture was stirred for 1 hr at room temperature and refluxed for 20 min.

After separating the product by filtration, the solvent was removed at normal pressure by simple distillation. The residue was distilled in vacuum to obtain 27.3 g of the compound 2 (yield: 83%).

Compound 2: $^1$H NMR (CDCl$_3$, 300 MHz), δ (ppm) 0.69 (t, J=8.3 Hz, 2 H, SiCH$_2$), 1.58-1.69 (m, 2 H, SiCH$_2$CH$_2$), 2.50 (t, J=7.5 Hz, 2 H, SiCH$_2$CH$_2$CH$_2$), 2.66 (t, J=7.2 Hz, 2 H, SCH$_2$CH$_2$O), 3.32 (s, 3 H, CH$_3$OCH$_2$), 3.51 (s, 9 H, CH$_3$OSi), 3.48-3.59 (m, 26 H, CH$_2$O).

EXAMPLE 3

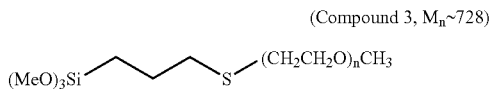
(Compound 3, M$_n$~728)

A 250 mL flask dried in an oven was equipped with a reflux condenser. To the flask were added 7.17 g (0.0365 mol) of (3-mercaptopropyl)trimethoxysilane and 100 mL of tetrahydrofuran under nitrogen atmosphere. The flask was cooled with ice water and stirred for 10 mn after adding 15.2 mL (0.0365 mol) of 2.40 M sodium methoxide solution. 17.3 g (0.0305 mol) of poly(ethylene glycol)methyl ether chloride (M$_n$~568) was added for 10 min and the temperature was increased to room temperature. The mixture was stirred for 1 hr at room temperature and refluxed for 2 hrs. Reflux was performed for 30 min after adding 0.942 g (0.0120 mol) of propyl chloride and the product was filtered. The solvent was removed in vacuum and stirring was performed after adding 50 mL of n-hexane to the residue. Then, the solution was cooled to –78° C. and filtered. After repeating this process for 4 times, the remaining solvent was completely removed in high vacuum to obtain 22.0 g of the compound 3 (yield: 99%).

Compound 3: $^1$H NMR (CDCl$_3$, 400 MHz), δ (ppm) 0.68 (t, J=8.2 Hz, 2 H, SiCH$_2$), 1.59-1.66 (m, 2 H, SiCH$_2$CH$_2$), 2.49 (t, J=7.4 Hz, 2 H, SiCH$_2$CH$_2$CH$_2$), 2.63 (t, J=7.2 Hz, 2 H, SCH$_2$CH$_2$O), 3.31 (s, 3 H, CH$_3$OCH$_2$), 3.50 (s, 9 H, CH$_3$OSi), 3.47-3.59 (m, 40 H, CH$_2$O).

EXAMPLE 4

(Compound 4)

A 500 mL flask dried in an oven was equipped with a reflux condenser. To the flask were added 29.9 g (0.141 mol) of (3-mercaptopropyl)trimethoxysilane and 250 mL of tetrahydrofuran under nitrogen atmosphere. The flask was cooled with ice water and stirred for 10 min after adding 58.9 mL (0.141 mol) of 2.40 M sodium methoxide solution. 12.0 g (0.0643 mol) of 1,2-bis(2-chloroethoxy)ethane was added for 10 min and the temperature was increased to room temperature. The mixture was stirred for 1 hr at room temperature and refluxed for 30 min. After separating the product by filtration, the solvent was removed at normal pressure. The residue was distilled in vacuum to obtain 28.0 g of the compound 4 (yield: 86%).

Compound 4: b.p. 185-7° C./0.5 mmHg; $^1$H NMR (CDCl$_3$, 400 MHz), δ (ppm) 0.69 (t, J=8.2 Hz, 4 H, SiCH$_2$), 1.60-1.68 (m, 4 H, SiCH$_2$CH$_2$), 2.51 (t, J=7.1 Hz, 4 H, SiCH$_2$CH$_2$CH$_2$), 2.64 (t, J=7.1 Hz, 4 H, SCH$_2$CH$_2$O), 3.51 (s, 18 H, CH$_3$OSi), 3.56 (s, 4 H, SCH$_2$CH$_2$OCH$_2$), 3.57 (t, 7.1 Hz, 4 H, SCH$_2$CH$_2$O).

EXAMPLE 5

(Compound 5, M$_n$~755)

A 250 mL flask dried in an oven was equipped with a reflux condenser. To the flask were added 13.2 g (0.0674 mol) of (3-mercaptopropyl)trimethoxysilane and 100 mL of tetrahydrofuran under nitrogen atmosphere. The flask was cooled with ice water and stirred for 10 min after adding 28.1 mL (0.0674 mol) of 2.40 M sodium methoxide solution. 12.2 g (0.0281 mol) of poly(ethylene glycol)bis(2-chloroethyl) ether (M$_n$~435) was added for 10 min and the temperature was increased to room temperature. The mixture was stirred for 1 hr at room temperature and refluxed for 3 hrs. Reflux was performed for 30 min after adding 0.99 mL (0.0112 mol) of propyl chloride and the product was filtered. The solvent was removed in vacuum and stirring was performed after adding 50 mL of n-hexane to the residue. Then, the solution was cooled to –78° C. and filtered. After repeating this process for 4 times, the remaining solvent was completely removed in high vacuum to obtain 21.1 g of the compound 5 (yield: 99%).

Compound 5: $^1$H NMR (CDCl$_3$, 400 MHz), δ (ppm) 0.69 (t, J=8.2 Hz, 4 H, SiCH$_2$), 1.61-1.68 (m, 4 H, SiCH$_2$CH$_2$), 2.51 (t, J=7.4 Hz, 4 H, SiCH$_2$CH$_2$CH$_2$), 2.65 (t, J=7.0 Hz, 4 H, SCH$_2$CH$_2$O), 3.52 (s, 18 H, CH$_3$OSi), 3.56-3.60 (m, 31 H, CH$_2$O).

EXAMPLE 6

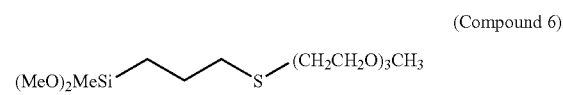
(Compound 6)

A 250 mL flask dried in an oven was equipped with a reflux condenser. To the flask were added 20.8 g (0.115 mol) of (3-mercaptopropyl)methyldimethoxysilane and 100 mL of tetrahydrofuran under nitrogen atmosphere. The flask was cooled with ice water and stirred for 10 min after adding 48.0 mL (0.0115 mol) of 2.40 M sodium methoxide solution. 20.4 g (0.112 mol) of tris(ethylene glycol)methyl ether chloride was added for 10 min and the temperature was increased to room temperature. The mixture was stirred for 1.5 hr at room temperature and refluxed for 30 min. After separating the product by filtration, the solvent was removed at normal pressure by simple distillation. The residue was distilled in vacuum to obtain 34.0 g of the compound 6 (yield: 91%).

Compound 6: b.p. 133-4° C./0.5 mmHg; $^1$H NMR (CDCl$_3$, 400 MHz), δ (ppm) 0.06 (s, 3 H, SiCH$_3$), 0.67 (t, J=8.4 Hz, 2 H, SiCH$_2$), 1.56-1.64 (m, 2 H, SiCH$_2$CH$_2$), 2.51 (t, J=7.2 Hz, 2 H, SiCH$_2$CH$_2$CH$_2$), 2.65 (t, J=7.2 Hz, 2 H, SCH$_2$CH$_2$O), 3.32 (s, 3 H, CH$_3$O), 3.45 (s, 6 H, CH$_3$OSi), 3.48-3.61 (m, 10 H, CH$_2$O).

EXAMPLE 7

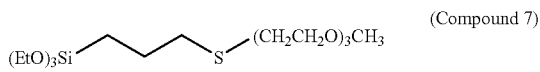

(Compound 7)

A 250 mL flask dried in an oven was equipped with a reflux condenser. To the flask were added 7.67 g (0.0322 mol) of (3-mercaptopropyl)trimethoxysilane and 50 mL of tetrahydrofuran under nitrogen atmosphere. The flask was cooled with ice water and stirred for 10 min after adding 13.4 mL (0.0322 mol) of 2.40 M sodium methoxide solution. 5.59 g (0.0306 mol) of tris(ethylene glycol)methyl ether chloride was added for 10 min and the temperature was increased to room temperature. The mixture was stirred for 2 hrs at room temperature and refluxed for 30 min. After separating the product by filtration, the solvent was removed at normal pressure by simple distillation. The residue was distilled in vacuum to obtain 10.9 g of the compound 7 (yield: 93%).

Compound 7: b.p. 154° C./0.5 mmHg; $^1$H NMR (CDCl$_3$, 400 MHz), δ (ppm) 0.63 (t, J=8.0 Hz, 2 H, SiCH$_2$), 3.72 (t, J=6.8 Hz, 9 H, CH$_3$CH$_2$O), 1.56-1.64 (m, 2 H, SiCH$_2$CH$_2$), 2.47 (t, J=7.2 Hz, 2 H, SiCH$_2$CH$_2$CH$_2$), 2.60 (t, J=6.8 Hz, 2 H, SCH$_2$CH$_2$O), 3.28 (s, 3 H, CH$_3$O), 3.44-3.56 (m, 10 H, CH$_2$O), 3.72 (quart, J=6.8 Hz, 6 H, CH$_3$CH$_2$O).

EXAMPLE 8

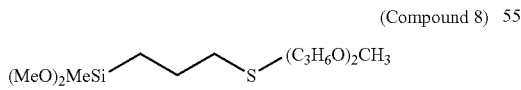

(Compound 8)

A 250 mL flask dried in an oven was equipped with a reflux condenser. To the flask were added 10.4 g (0.0577 mol) of (3-mercaptopropyl)methyldimethoxysilane and 80 mL of tetrahydrofuran under nitrogen atmosphere. The flask was cooled with ice water and stirred for 10 min after adding 24.0 mL (0.0577 mol) of 2.40 M sodium methoxide solution. 9.33 g (isomer mixture, 0.0560 mol) of di(propylene glycol) methyl ether chloride was added for 10 min and the temperature was increased to room temperature. The mixture was stirred for 24 hrs at room temperature and the product was separated by filtration. The solvent was removed at normal pressure and the residue was distilled in vacuum to obtain 10.7 g of the compound 8 (yield: 61%).

Compound 8: b.p. 101-4° C./0.5 mmHg; $^1$H NMR (CDCl$_3$, 400 MHz), δ (ppm) 0.08 (s, 3 H, SiCH$_3$), 0.67-0.71 (m, 2 H, SiCH$_2$), 1.11-1.13 (m, 3 H, CHCH$_3$), 1.24 (d, J=6.7 Hz, CHCH$_3$), 1.58-1.66 (m, 2 H, SiCH$_2$CH$_2$), 2.49-2.62 (m, 2 H, SiCH$_2$CH$_2$CH$_2$), 2.86-2.95 (m, 1 H, SiCH$_2$CH$_2$CH$_2$SCH$_2$), 3.31-3.56 (m, 14 H, CH$_3$O, CH$_3$OSi, CH$_2$O, CH$_3$CHO).

EXAMPLE 9

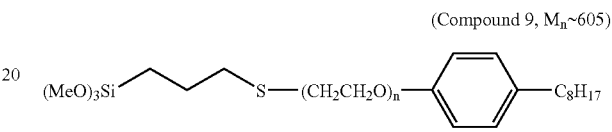

(Compound 9, M$_n$~605)

A 250 mL flask dried in an oven was equipped with a reflux condenser. To the flask were added 6.20 g (0.0316 mol) of (3-mercaptopropyl)trimethoxysilane and 100 mL of tetrahydrofuran under nitrogen atmosphere. The flask was cooled with ice water and stirred for 10 min after adding 13.2 mL (0.0316 mol) of 2.40 M sodium methoxide solution. 11.7 g (0.0264 mol) of poly(ethylene glycol) 4-isooctylphenyl ether chloride (M$_n$~445, chlorination product of Igepal CA-520 of Aldrich) was added for 10 min and the temperature was increased to room temperature. The mixture was stirred for 2 hrs at room temperature and refluxed for 3 hrs. Reflux was performed for 30 min after adding 0.94 mL (0.0106 mol) of propyl chloride and the product was filtered. The solvent was removed in vacuum and stirring was performed after adding 50 mL of n-hexane to the residue. Then, the solution was cooled to −78° C. and filtered. After repeating this process for 4 times, the remaining solvent was completely removed in high vacuum to obtain 13.25 g of the compound 9 (yield: 84%).

Compound 9: $^1$H NMR (CDCl$_3$, 400 MHz), δ (ppm) 0.68 (s, 9 H, (CH$_3$)$_3$CCH$_2$C(CH$_3$)$_2$), 0.73 (t, J=8.2 Hz, 2 H, SiCH$_2$), 1.31 (s, 6 H, (CH$_3$)$_3$CCH$_2$C(CH$_3$)$_2$), 1.60-1.71 (m, 4 H, SiCH$_2$CH$_2$, (CH$_3$)$_3$CCH$_2$C(CH$_3$)$_2$), 2.54 (t, J=7.4 Hz, 2 H, SiCH$_2$CH$_2$CH$_2$), 2.67 (t, J=7.0 Hz, 2 H, SCH$_2$CH$_2$O), 3.49-4.09 (m, 25 H, CH$_3$OSi, CH$_2$O), 6.80 (d, J=8.6 Hz, 2 H, C$_6$H$_4$), 7.23 (d, J=8.6 Hz, 2 H, C$_6$H$_4$).

EXAMPLE 10

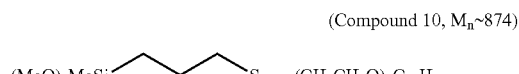

(Compound 10, M$_n$~874)

A 250 mL flask dried in an oven was equipped with a reflux condenser. To the flask were added 1.29 g (7.18 mol) of (3-mercaptopropyl)methyldimethoxysilane and 40 mL of tetrahydrofuran under nitrogen atmosphere. The flask was cooled with ice water and stirred for 10 min after adding 2.99 mL (7.18 mol) of 2.40 M sodium methoxide solution. 5.24 g (7.18 mol) of poly(ethylene glycol)stearyl ether chloride (M$_n$ 730, chlorination product of Brij 76 of Aldrich)

dissolved in 40 mL of tetrahydrofuran was added for 10 min and the temperature was increased to room temperature. The mixture was stirred for 20 min at room temperature and was refluxed for 1 hr. The product was filtered and the solvent was removed. The remaining solvent was completely removed in high vacuum to obtain 6.28 g of the compound 10 (yield: 100%).

Compound 10: $^1$H NMR (CDCl$_3$, 400 MHz), δ (ppm) 0.08 (s, 3 H, SiCH$_3$), 0.84 (t, J=6.4 Hz, 3 H, CH$_2$C$_{16}$H$_{32}$CH$_3$), 0.67-0.71 (m, 2 H, SiCH$_2$), 1.21 (br s, 32 H, CH$_2$C$_{16}$H$_{32}$CH$_3$), 1.50-1.57 (m, 2 H, CH$_2$C$_{16}$H$_{32}$CH$_3$), 1.58-1.66 (m, 2 H, SiCH$_2$CH$_2$), 2.52 (t, J=7.2 Hz, 2 H, SiCH$_2$CH$_2$CH$_2$), 2.66 (t, J=7.2 Hz, 2 H, SCH$_2$CH$_2$O), 3.47 (s, 6 H, CH$_3$OSi), 3.39-3.78 (m, 40 H, CH$_2$ O).

EXAMPLE 11

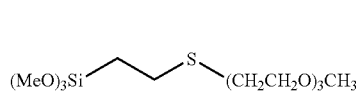

(Compound 11)

A 250 mL flask dried in an oven was equipped with a reflux condenser. To the flask were added 10.5 g (0.0576 mol) of (2-mercaptopropyl)trimethoxysilane and 70 mL of tetrahydrofuran under nitrogen atmosphere. The flask was cooled with ice water and stirred for 10 min after adding 24.0 mL (0.0576 mol) of 2.40 M sodium methoxide solution. 10.5 g (0.0576 mol) of tris(ethylene glycol)methyl ether chloride was added for 10 min and the temperature was increased to room temperature. The mixture was stirred for 1.3 hrs at room temperature and was refluxed for 30 min. The product was filtered and the solvent was removed at normal pressure by simple distillation. The remaining solvent was removed in vacuum to obtain 18.2 g of the compound 11 (yield: 96%).

Compound 11: b.p. 137-9° C./0.5 mmHg; $^1$H NMR (CDCl$_3$, 400 MHz), δ (ppm) 0.93 (t,=9.0 Hz, 2 H, SiCH$_2$), 2.60 (t, J=9.0 Hz, 2 H, SiCH$_2$CH$_2$), 2.66 (t, J=7.0 Hz, 2 H, SCH$_2$CH$_2$O), 3.32 (s, 3 H, CH$_3$O), 3.51 (s, 9 H, CH$_3$OSi), 3.48-3.60 (m, 10 H, CH$_2$O).

INDUSTRIAL APPLICABILITY

As apparent from the above description, the novel synthesis method of hydrophilic organic alkylalkoxysilanes of the present invention introduces the poly(alkyleneoxy) group using sulfur, differently from conventional methods. The present invention is characterized in that a hydrophilic organosilane compound having an alkyleneoxy group with novel structure can be prepared from S—C bonding formation by dehalometallation of a silylalkylthiolate metal salt, which is prepared from a (ω-mercaptoalkyl)alkylalkoxysilane compound having a sulfur atom treating it with a metallic base, and a poly(alkyleneoxy)alkyl ether halide or poly(alkyleneoxy)bis(haloalkyl) ether compound. The preparation method of the present invention is advantageous in industrial production of ω-[2-(polyalkyleneoxy)ethylthio] alkylalkoxysilane derivatives since it is economical with good production yield and requires a mild reaction condition. Also, since the novel ω-[2-(polyalkyleneoxy)ethylthio] alkylalkoxysilane derivatives of the present invention have hydrolyzable alkoxy groups, they can be coated on the surface of such inorganic materials as silica or alumina by chemical bonding, and thus make useful compounds for surface modification of organic and inorganic materials. In addition, they can be easily transformed into hydrophilic siloxane polymers through hydrolysis.

Even though the present invention is described in detail with reference to the foregoing embodiments, it is not intended to limit the scope of the present invention thereto. It is evident from the foregoing that many variations and modifications may be made by a person having an ordinary skill in the present field without departing from the essential concept of the present invention.

What is claimed is:

1. A novel ω-[2-(polyalkyleneoxy)ethylthio]alkylalkoxysilane derivative represented by the following formula 1:

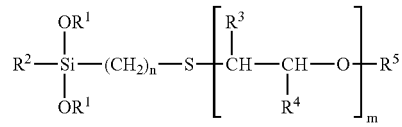

Wherein R$^1$ is C$_1$-C$_6$ alkyl or phenyl; R$^2$ is C$_1$-C$_6$ alkyl, C$_1$-C$_6$ alkoxy, phenyl or phenoxy; each of R$^3$ and R$^4$ is hydrogen or C$_1$-C$_6$ alkyl; R$^5$ is alkyl having an aromatic group, or —CH$_2$CH$_2$S(CH$_2$)$_n$SiR$^2$(OR$^1$)$_2$; n is an integer of 2 or 3; and m is an integer of 1 to 1,000.

2. The compound of claim 1, wherein R$^1$ is C$_1$-C$_6$ alkyl; R$^2$ is C$_1$-C$_6$ alkyl or C$_1$-C$_6$ alkoxy; each of R$^3$ and R$^4$ is hydrogen or methyl; R$^5$ is C1-C$_{18}$ alkyl-substituted phenyl or —CH$_2$CH$_2$S(CH$_2$)$_n$SiR$^2$(OR$^1$)$_2$; n is an integer of 2 or 3; and m is an integer of 1 to 1,000.

3. A method for preparing the ω-[2-(polyalkyleneoxy) ethylthio]alkylalkoxysilane derivative represented by the following formula 1 below comprising:

(a) transforming the (ω-mercaptoalkyl)alkylalkoxysilane compound represented by the formula 2 below into ω-(alkoxysilyl)alkylthiolate metal salt represented by the formula 3 below by reacting it with a metallic base of an alkali metal or alkaline earth metal; and (b) dehalometallating the ω-(alkoxysilyl)alkylthiolate metal salt with the poly(alkyleneoxy)alkyl ether halide represented by the formula 4 below or the poly(alkyleneoxy)bis(haloalkyl) ether represented by the formula 5 below:

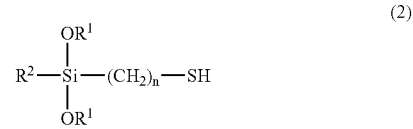

(2)

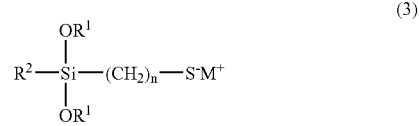

(3)

-continued

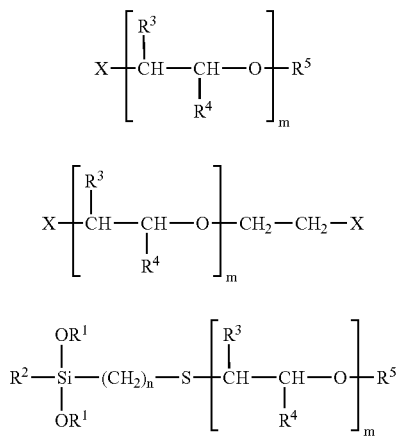

wherein $R^1$ is $C_1$-$C_6$ alkyl or phenyl; $R^2$ is $C_1$-$C_6$ alkyl, $C_1$-$C_6$ alkoxy, phenyl or phenoxy; each of $R^3$ and $R^4$ is hydrogen or $C_1$-$C_6$ alkyl; $R^5$ is $C_1$-$C_{18}$ alkyl, alkyl having an aromatic group, $C_3$-$C_8$ cyclic alkyl, $C_2$-$C_{18}$ alkene having an unsaturated bond or —$CH_2CH_2S(CH_2)_nSiR^2(OR^1)_2$; n is an integer of 2 or 3; and m is an integer of 1 to 1,000; and M represents an alkali metal or alkaline earth metal atom.

4. The preparation method of claim 3, wherein the metallic base is used in the amount of from 0.4 to 1.2 moles per 1 mole of the ω-mercaptoalkyl)alkylalkoxysilane compound represented by formula 2.

5. The preparation method of claim 3, wherein the poly (alkyleneoxy)alkyl ether halide represented by formula 4 is used in the amount of from 0.4 to 1.2 moles per 1 mole of the (ω-mercaptoalkyl)alkyalkoxysilane compound resented by the formula 2.

6. The preparation method of claim 3, wherein the dehalometallation is performed at a temperature of −100 Degree C. to 150 Degree C.

7. The preparation method of claim 3, wherein the dehalometallation is performed using a polar solvent selected from the group consisting of an alcohol, tetrahydrofuran, acetonitrile and diethyl ether.

* * * * *